(12) United States Patent
Böttcher et al.

(10) Patent No.: US 6,251,908 B1
(45) Date of Patent: Jun. 26, 2001

(54) PIPERAZINE DERIVATIVES

(75) Inventors: Henning Böttcher; Gerd Bartoszyk; Hartmut Greiner; Christoph Seyfried, all of Darmstadt (DE)

(73) Assignee: Merck Patent Gesellschaft mit beschraenkter Haftung, Darmstadt (DE)

( * ) Notice: Subject to any disclaimer, the term of this patent is extended or adjusted under 35 U.S.C. 154(b) by 0 days.

(21) Appl. No.: 09/462,468

(22) PCT Filed: Jun. 29, 1998

(86) PCT No.: PCT/EP98/03956

§ 371 Date: Apr. 3, 2000

§ 102(e) Date: Apr. 3, 2000

(87) PCT Pub. No.: WO99/03855

PCT Pub. Date: Jan. 28, 1999

(30) Foreign Application Priority Data

Jul. 18, 1997 (DE) .............................. 197 30 989

(51) Int. Cl.⁷ ...................... C07D 405/14; A61K 31/496
(52) U.S. Cl. ...................... 514/254.09; 544/373
(58) Field of Search ................... 544/373; 514/254.09

(56) References Cited

U.S. PATENT DOCUMENTS 5,532,241 * 7/1996 Bottcher et al. ................. 514/254

FOREIGN PATENT DOCUMENTS

| 2 189 027 | 1/1974 | (FR) . |
| 98 04542 | 2/1998 | (WO) . |
| 99/05140 * | 2/1999 | (WO) . |

* cited by examiner

*Primary Examiner*—Emily Bernhardt
(74) *Attorney, Agent, or Firm*—Millen, White, Zelano & Branigan, P.C.

(57) ABSTRACT

Piperazine derivatives of the formula I

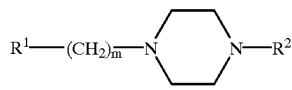

in which $R^1$, m, k and $R^2$ have the meanings indicated in claim 1, are potent 5-$HT_{1A}$ agonists and exhibit 5-HT-reuptake-inhibiting actions and are suitable for the treatment and prophylaxis of anxiety states, depression, schizophrenia, obsessions, tardive dyskinesias, learning disorders, age-dependent memory disorders, for positively affecting obsessive-compulsive disorder, and also for the treatment and for the control of the sequelae of cerebral infarcts such as stroke and cerebral ischaemias.

19 Claims, No Drawings

PIPERAZINE DERIVATIVES

The invention relates to piperazine derivatives of the formula I

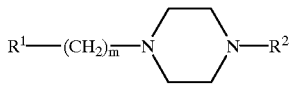

in which

R$^1$ is an indol-3-yl radical which is unsubstituted or mono- or disubstituted by Hal, CN, A, AO, OH, CONH$_2$, CONHA, CONA$_2$, COOH, COOA, CH$_2$OH, CH$_2$OA, CH$_2$NH$_2$, CH$_2$NHA and/or CH$_2$NA$_2$, R$^2$ is 2-oxo-2H-1-benzopyran-6-yl or 2-oxo-2H-1-benzopyran-4-yl, which is unsubstituted or mono- or disubstituted by A, AO, OH, Hal, CN, NO$_2$, NH$_2$, NHA, NA$_2$, COA, CONH$_2$, CONHA, CONA$_2$, CH$_2$OH, CH$_2$OA, CH$_2$NH$_2$, CH$_2$NHA, CH$_2$NA$_2$, COOH and/or COOA, Hal is F, Cl, Br or I, A is straight-chain or branched alkyl having 1–10 C atoms, which can be substituted by 1 to 5 F and/or Cl atoms, or is cycloalkyl having 3–10 C atoms, m is 2, 3 or 4 and their physiologically acceptable salts.

The invention was based on the object of finding novel compounds having valuable properties, in particular those which can be used for the production of medicaments.

It has been found that the compounds of the formula I and their physiologically acceptable acid addition salts have valuable pharmacological properties. The compounds of the formula I affect serotonin-ergic transmission. Since the compounds also inhibit serotonin reuptake, they are suitable, in particular, as antidepressants and anxiolytics. The compounds exhibit serotonin-agonistic and -antagonistic properties ties. They inhibit the binding of tritiated serotonin ligands to hippocampal receptors (Cossery et al., European J. Pharmacol. 140 (1987), 143–155) and inhibit synaptosomal serotonin reuptake (Sherman et al., Life Sci. 23 (1978), 1863–1870). Additionally, changes in DOPA accumulation in the striatum and 5-HT accumulation in various brain regions occur (Seyfried et al., European J. Pharmacol. 160 (1989), 31–41). The 5-HT$_{1A}$-antagonistic action is demonstrated in vitro, for example, by inhibition of the abolition of the electrically induced contraction of the guinea-pig ileum caused by 8-OH-DPAT (Fozard and Kilb-nger, Br. J. Pharmacol. 86 (1985) 601P). Ex-vivo, the inhibition of the 5-HTP accumulation decreased by 8-OH-DPAT serves for the demonstration of the 5-HT$_{1A}$ antagonistic action (Seyfried et al., European J. Pharmacol. 160 (1989), 31–41) and the antagonism of the effects induced by 8-OH-DPAT in the ultrasonic vocalization test (DeVry, Dsychpharmacol. 121 (1995), 1–26). For the ex-vivo demonstration of serotonin reuptake inhibition, synaptosomal uptake inhibition (Wong et al., Neuropsychopharmacol. 8 (1993), 23–33) and p-chloro-amphetamine antagonism (Fuller et al., J. Pharmacol. Exp. Ther. 212 (1980), 115–119) are used. Furthermore, analgesic and hypotensive actions occur.

The compounds are therefore suitable for the treatment of schizophrenia, cognitive deficits, anxiety, depression, nausea, tardive dyskinesias, gastrointestinal tract disorders, learning disorders, age-dependent memory disorders, psychoses and for positively affecting obsessive-compulsive disorder (OCD) and eating disorders (e.g. bulimia). They exhibit actions on the central nervous system, especially additional 5-HT$_{1A}$-agonistic and 5-HT-reuptake-inhibiting actions. They are also suitable for the prophylaxis and for the control of the sequelae of cerebral infarcts (cerebral apoplexy) such as stroke and cerebral ischaemias, and for the treatment of extrapyramidal motor side effects of neuroleptics and of Parkinson's disease.

The compounds of the formula I are therefore suitable both in veterinary and in human medicine for the treatment of functional disorders of the central nervous system and of inflammation. They can be used for the prophylaxis and for the control of the sequelae of cerebral infarcts (cerebral apoplexy) such as stroke and cerebral ischaemias and for the treatment of extrapyramidal/motor side effects of neuroleptics and of Parkinson's disease, for the acute and symptomatic therapy of Alzheimer's disease and for the treatment of amyotrophic lateral sclerosis. Likewise, they are suitable as therapeutics for the treatment of brain and spinal cord traumata. However, they are also suitable as pharmaceutical active compounds for anxiolytics, antidepressants, antipsychotics, neuroleptics, anti-hypertensives and/or for positively affecting obsessive-compulsive disorder, sleep disorders, tardive dyskinesias, learning disorders, age-dependent memory disorders, eating disorders such as bulimia and/or sexual function disorders.

The invention relates to piperazine derivatives of the formula I and to their physiologically acceptable acid addition salts.

The invention relates in particular to compounds of the formula I selected from the group a) 3-{4-[4-(2-oxo-2H-1-benzopyran-6-yl)-1-piperazinyl]butyl}indole-5-carbonitrile;

b) 3-{4-[4-(2-oxo-2H-1-benzopyran-6-yl)-1-piperazinyl]butyl}-5-fluoroindole;

c) 3-{4-[4-(2-oxo-2H-1-benzopyran-4-yl)-1-piperazinyl]butyl}indole-5-carbonitrile;

d) 3-{4-[4-(7-hydroxy-2-oxo-2H-1-benzopyran-6-yl)-1-piperazinyl]butyl}indole-5-carbonitrile;

and their physiologically acceptable salts.

For all radicals which occur several times, such as, for example, A, it is a condition that their meanings are independent of one another.

The radical A is alkyl and has 1 to 10, preferably 1, 2, 3, 4, 5 or 6, in particular 1 or 2, C atoms. Alkyl is therefore in particular, for example, methyl, furthermore ethyl, n-propyl, isopropyl, n-butyl, sec-butyl or tert-butyl and further also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, and further also fluoromethyl, difluoromethyl, trifluoromethyl, 1,1,1-trichloroethyl or pentafluoroethyl.

Cycloalkyl is in particular, for example, cyclopropyl, cyclobutyl, cyclopentyl, cyclohexyl, cycloheptyl or 1-adamantyl.

OA is preferably methoxy, and further also ethoxy, n-propoxy, isopropoxy, n-butoxy, isobutoxy, sec-butoxy or tert-butoxy. NHA is preferably methylamino, and further ethylamino, isopropylamino, n-butylamino, isobutylamino, sec-butylamino or tert-butylamino. NA$_2$ is preferably dimethylamino, and further N-ethyl-N-methylamino, diethylamino, di-n-propylamino, diisopropylamino or di-n-butylamino. As a result of this, CO-NHA iS preferably N-methylcarbamoyl or N-ethylcarbamoyl; CO-NA$_2$ is preferably N,N-dimethylcarbamoyl or N,N-diethylcarbamoyl.

Hal is fluorine, chlorine, bromine or iodine, in particular fluorine or chlorine. k is 0 or 1, preferably 0. m is 1, 2, 3 or 4, in particular 3 or 4.

The radical $R^1$ is preferably 3-indolyl which is unsubstituted or mono- or disubstituted, but in particular monosubstituted, by Hal, CN, A, AO, OH, $CONH_2$, CONHA, $CONA_2$, COOH, COOA, $CH_2OH$, $CH_2OA$, $CH_2NH_2$, $CH_2NHA$ and/or $CH_2NA_2$. Preferably, the indole radical is substituted in the 5-position, and further also in the 6- or 7-position.

$R^1$ is therefore preferably 2- or 3-indolyl, 5- or 6-methylindol-2-yl, 5- or 6-methylindol-3-yl, 5- or 6-methoxyindol-2-yl, 5- or 6-methoxyindol-3-yl, 5- or 6-hydroxyindol-2-yl, 5- or 6-hydroxyindol-3-yl, 5- or 6-fluoroindol-2-yl, 5- or 6-fluoroindol-3-yl, 5- or 6-cyanoindol-2-yl, 5- or 6-cyanoindol-3-yl, 5- or 6-chloroindol-2-yl, 5- or 6-chloroindol-3-yl, 5- or 6-carboxyindol-2-yl, 5- or 6-carboxyindol-3-yl, 5- or 6-methoxycarbonylindol-2-yl, 5- or 6-methoxycarbonylindol-3-yl, 5- or 6-hydroxymethylindol-2-yl, 5- or 6-hydroxymethylindol-3-yl, 5- or 6-aminomethylindol-2-yl, 5- or 6-aminomethylindol-3-yl, and further 5- or 6-bromoindol-2-yl, 5- or 6-bromoindol-3-yl, 5- or 6-ethylindol-2-yl, 5- or 6-ethylindol-3-yl, 5- or 6-trifluoromethylindol-2-yl, 5- or 6-trifluoromethylindol-3-yl, 5- or 6-isopropylindol-2-yl, 5- or 6-isopropylindol-3-yl, 5- or 6-dimethylaminoindol-3-yl or 6-dimethylaminoindol-2-yl, 5- or 6-ethoxyindol-3-yl or 5- or 6-ethoxyindol-2-yl.

The radical $R^2$ is preferably 2-oxo-2H-1-benzopyran-6-yl or 2-oxo-2H-1-benzopyran-4-yl, which is unsubstituted or monosubstituted by A, AO, OH, Hal, CN, NO2, $NH_2$, NHA, $NA_2$, COA, $CONH_2$, CONHA, $CONA_2$, $CH_2OH$, $CH_2OA$, $CH_2NH_2$, $CH_2NHA$, $CH_2NA_2$, COOH and/or COOA. Preferably, possible substituents are A, AO, OH, Hal, CN, $NH_2$, NHA, $NA_2$ or alternatively $CH_2OH$.

$R^2$ is therefore preferably 2-oxo-2H-1-benzopyran-6-yl or 2-oxo-2H-1-benzopyran-4-yl, 7-hydroxy-2-oxo-2H-1-benzopyran-6-yl, 7-hydroxy-2-oxo-2H-1-benzopyran-4-yl, 7-fluoro-2-oxo-2H-1-benzopyran-6-yl, 7-fluoro-2-oxo-2H-1-benzopyran-4-yl, 5-fluoro-2-oxo-2H-1-benzopyran-6-yl, 6-fluoro-2-oxo-2H-1-benzopyran-4-yl, 5-methyl-2-oxo-2H-1-benzopyran-4-yl, 7-methyl-2-oxo-2H-1-benzopyran-6-yl, 7-dimethylamino-2-oxo-2H-1-benzopyran-6-yl, 7-hydroxymethyl-2-oxo-2H-1-benzopyran-6-yl or alternatively 7-chloro-2-oxo-2H-1-benzopyran-6-yl.

For the entire invention, it is a condition that all radicals which can occur several times in a molecule can be identical or different, i.e. are independent of one another.

Accordingly, the invention relates in particular to those compounds of the formula I in which at least one of the radicals mentioned has one of the preferred meanings indicated above. Some preferred groups of compounds can be expressed by the formulae Ia to Ij below, which correspond to the formula I and in which the radicals not designated in greater detail have the meaning indicated under the formula I, but in which in Ia $R^7$ is unsubstituted 3-indolyl;

in Ib $R^1$ is 3-indolyl substituted in the 5-position;

in Ic k is 0 and m is 4;

in Id k is 1 and m is 3;

in Ie $R^1$ has a meaning indicated in Ib and the substituent is Hal, methoxycarbonyl, CN or carboxyl;

in If $R^2$ is 2-oxo-2H-1-benzopyran-6-yl;

in Ig $R^2$ is 2-oxo-2H-1-benzopyran-4-yl;

in Ih $R^2$ has a meaning indicated in If, a further substituent being present in position 7;

in Ii $R^2$ has a meaning indicated in Ig, a further substituent being present in position 7;

in Ij $R^2$ has a meaning indicated in Ih or Ii, and the substituent is Hal or OH.

The invention further relates to a process for the preparation of piperazine derivatives of the formula I and of their salts, characterized in that a compound of the formula II

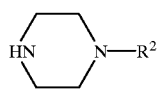

II in which $R^2$ has the meaning indicated, is reacted with a compound of the formula III

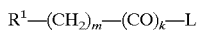

III in which

L is Cl, Br, I, OH, OCOA, OCOPh, $OSO_2A$, $OSO_2Ar$, where Ar is phenyl or tolyl and A is alkyl, or another reactive esterified OH group or easily nucleophilically substitutable leaving group and $R^1$, m and k have the meanings indicated, or in that, in a reductive animation, a compound of the formula IV

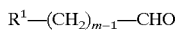

IV in which $R^1$ and m have the meanings already indicated, is reacted with a compound of the formula II, or in that a compound otherwise corresponding to the formula I, but which instead of one or more hydrogen atoms contains one or more reducible groups and/or one or more additional C—C and/or C—N bonds, is treated with a reducing agent, or in that a compound which otherwise corresponds to the formula I, but which instead of one or more hydrogen atoms contains one or more solvolysable groups, is treated with a solvolysing agent, and/or in that a radical $R^1$ and/or $R^2$ is optionally converted into another radical $R^1$ and/or $R^2$ by, for example, cleaving an OA group with formation of an OH group and/or derivatizing a CN, COOH or COOA group and/or in that, for example, a primary or secondary N atom is alkylated and/or in that a resulting base or acid of the formula I is converted into one of its salts by treating with an acid or base.

The compounds of the formula I are otherwise prepared by methods known per se, such as are described in the literature (e.g. in standard works such as Houben-Weyl, Methoden der Organischen Chemie [Methods of Organic Chemistry], Georg Thieme Verlag, Stuttgart; Organic Reactions, John Wiley & Sons, Inc., New York; DE-A 41 01 686), namely under reaction conditions such as are known and suitable for the reactions mentioned. Use can also be made in this case of variants which are known per se, but not mentioned here in greater detail.

If desired, the starting substances for the claimed process can also be formed in situ in such a way that they are not isolated from the reaction mixture, but immediately reacted further to give the compounds of the formula I.

In the compounds of the formulae III, V and VI, the radicals L, $X^1$ and $X^2$ are preferably Cl or Br; however, they can also be I, OH or alternatively preferably a reactive functionally modified OH group, in particular alkylsulfonyloxy having 1–6 C atoms (e.g. methanesulfonyloxy) or arylsulfonyloxy having 6–10 C atoms (e.g. benzenesulfonyloxy, p-toluenesulfonyloxy, 1- or 2-naphthylenesulfonyloxy).

As a rule, the starting substances of the formulae II and III are known; the unknown compounds of the formulae II and III can easily be prepared analogously to the known compounds.

The piperazine derivatives of the formula II are for the most part known. If they are not commercially available or known, they can be prepared by methods known per se. They can be prepared, for example, by reaction of bis(2-chloroethyl)amine or bis (2-chloroethyl)ammonium chloride with amino-substituted benzopyran compounds.

The indole derivatives of the formula III are for the most part known and in some cases also commercially available. The compounds can furthermore be prepared by electrophilic or, in certain cases, also nucleophilic aromatic substitution of known compounds. The starting substance used is preferably an appropriate indole-3-alkanoic acid (which can be prepared analogously to a Japp-Klingemann type Fischer indole synthesis, for this see Böttcher et al., J. Med. Chem. 1992, 35, 4020–4026 or Iyer et al., J. Chem. Soc. Perkin Trans. II 1973, 872–878). Primary alcohols of the formula $R^1-(CH_2)_m-OH$ are obtainable, for example, by reduction of the corresponding carboxylic acids or their esters. Treating with thionyl chloride, hydrogen bromide, phosphorus tribromide or similar halogen compounds gives the corresponding halides of the formula $R^2-(CH_2)_m-Hal$. The corresponding sulfonyloxy compounds are obtainable from the alcohols by reaction with the appropriate sulfonyl chlorides.

The iodo compounds of the formula $R^1-(CH_2)_m-I$ are obtainable, for example, by action of potassium iodide on the appropriate p-toluenesulfonic acid esters. The amines of the formula $R^1-(CH_2)_m-NH_2$ can be prepared, for example, from the halides with potassium phthalimide or by reduction of the corresponding nitriles.

The reaction of the compounds II and III proceeds according to methods such as are known from the literature for the alkylation or acylation of amines. The components can be fused with one another without the presence of a solvent, if appropriate in a closed tube or in an autoclave. However, it is also possible to react the compounds in the presence of an indifferent solvent. Suitable solvents are, for example, hydrocarbons, such as benzene, toluene, xylene; ketones such as acetone, butanone; alcohols such as methanol, ethanol, isopropanol, n-butanol; ethers such as tetrahydrofuran (THF) or dioxane; amides such as dimethylformamide (DMF) or N-methylpyrrolidone; nitriles such as acetonitrile, and optionally also mixtures of these solvents with one another or mixtures with water. The addition of an acid-binding agent, for example of an alkali metal or alkaline earth metal hydroxide, carbonate or bicarbonate or of another salt of a weak acid of the alkali metals or alkaline earth metals, preferably of potassium, sodium or calcium, or the addition of an organic base such as triethylamine, dimethylaniline, pyridine or quinoline or of an excess of piperazine derivatives of the formula II can be favourable. Depending on the conditions used, the reaction time is between a few minutes and 14 days; the reaction temperature is between approximately 0 and 150°, normally between 20 and 130°.

It may be necessary before carrying out this reaction to protect other amino groups present from alkylation or acylation by introduction of suitable protective groups. The expression amino protective group is generally known and refers to groups which are suitable to protect an amino group from chemical reactions, but which are easily removable after the desired chemical reaction has been carried out at another position in the molecule. Since such protective groups and the introduction and removal of these is known to the person skilled in the art from numerous references and textbooks, these do not have to be discussed in greater detail here.

Compounds of the formula I can furthermore be obtained by reductive amination of compounds of the formula IV with compounds of the formula II. The starting substances of the formulae IV and II are known in some cases. If they are not known, they can be prepared by methods known per se. The reductive amination can be carried out in the presence of reducing agents such as, for example, $NaBH_3CN$ and $NaBH(OAc)_3$.

It is further possible to obtain a compound of the formula I by treating a precursor which, instead of hydrogen atoms, contains one or more reducible groups and/or one or more additional C—C and/or C—N bonds, with a reducing agent, preferably at temperatures between −80 and +250°, in the presence of at least one inert solvent. Groups which are reducible (replaceable by hydrogen) are, in particular, oxygen in a carbonyl group, hydroxyl, arylsulfonyloxy (e.g. p-toluene-sulfonyloxy), N-benzenesulfonyl, N-benzyl or O-benzyl.

In principle, it is possible to convert compounds which only contain one or those which, next to one another, contain two or more of the above-mentioned groups or additional bonds reductively to a compound of the formula I; in this case substituents in the group I which are present in the starting compound can simultaneously be reduced. Preferably, for this purpose use is made of nascent hydrogen or complex metal hydrides, and further Wolff-Kishner reduction and reductions using hydrogen gas with transition metal catalysis.

If nascent hydrogen is used as a reducing agent, this can be generated, for example, by treatment of metals with weak acids or with bases. Thus, for example, a mixture of zinc with alkali metal hydroxide solution or of iron with acetic acid can be used. The use of sodium or another alkali metal dissolved in an alcohol such as ethanol, isopropanol, butanol, amyl or isoamyl alcohol or phenol is also suitable. It is further possible to use an aluminium-nickel alloy in alkaline-aqueous solution, if appropriate with addition of ethanol. Sodium or aluminium amalgam in aqueous-alcoholic or aqueous solution is also suitable for the generation of the nascent hydrogen. The reaction can also be carried out in a heterogeneous phase, an aqueous and a benzene or toluene phase expediently being used.

Reducing agents which can furthermore be particularly advantageously used are complex metal hydrides, such as $LiAlH_4$, $NaBH_4$, diisobutylaluminium hydride or $NaAl(OCH_2CH_2OCH_3)_2H_2$ and also diborane, if desired with addition of catalysts such as $BrF_3$, $AlCl_3$ or LiBr. Suitable solvents for this purpose are, in particular, ethers such as diethyl ether, di-n-butyl etherf THF, dioxane, diglyme or 1,2-dimethoxyethane and also hydrocarbons such as benzene. For reduction with $NaBH_4$, alcohols such as methanol or ethanol, and further water and aqueous alcohols, are primarily suitable as solvents. According to these methods, the reduction is preferably carried out at temperatures between −80 and +150°, in particular between approximately 0 and approximately 100°.

Moreover, it is possible to carry out certain reductions by the use of $H_2$ gas under tie catalytic action of transition metals, such as, for example, Raney Ni or Pd. It is possible in this manner, for example, to replace Cl, Br, I, SH or, in certain cases, also OH groups by hydrogen. Likewise, nitro groups can be converted into $NH_2$ groups by catalytic hydrogenation using $Pd/H_2$ in methanol.

Compounds which otherwise correspond to the formula I, but instead of one or more H atoms contain one or more solvolysable groups, can be solvolysed, in particular hydrolysed, to the compounds of the formula I.

Furthermore, a compound of the formula I can be converted by methods known per se into another compound of the formula I.

Compounds of the formula I in which $R^1$ is a radical substituted by $CONH_2$, CONHA or $CONA_2$ can be obtained by derivatization of appropriate substituted compounds of the formula I by partial hydrolysis. It is further possible to hydrolyse cyano-substituted compounds of the formula I first to acids and to amidate the acids using primary or secondary amines. The reaction of the free carboxylic acid with the amine under the conditions of a peptide synthesis is preferred. This reaction is preferably carried out in the presence or a dehydrating agent, e.g. of a carbodiimide such as dicyclohexylcarbodiimide or N-(3-dimethylaminopropyl)-N-ethylcarbodiimide, and further propanephosphonic anhydride (cf. Angew. Chem. 92, 129 (1980)), diphenylphosphoryl azide or 2-ethoxy-N-ethoxycarbonyl-1,2-dihydroquinoline, in an inert solvent, e.g. a halogenated hydrocarbon such as dichloromethane, an ether such as THF or dioxane, an amide such as DMF or dimethylacetamide, or a nitrile such as acetonitrile, at temperatures between approximately −10 and 40° C., preferably between 0 and 30°. Instead of the acid or the amide, it is also possible to employ reactive derivatives of these substances in the reaction, e.g. those in which reactive groups are intermediately blocked by protective groups.

The acids can also be used in the form of their activated esters, which are expediently formed in situ, e.g. by addition of 1-hydroxybenzotriazole or N-hydroxysuccinimide.

Thus it is also possible, for example, to hydrolyse cyano-substituted indole radicals to carboxyindole or carboxamidoindole radicals.

It is particularly favourable, however, also to prepare the nitriles conversely, by dehydration, starting from the amides, e.g. by means of trichloroacetyl chloride/$Et_3N$ (Synthesis (2), 184 (1985)) or using $POCl_3$ (J. Org. Chem. 26, 1003 (1961)).

A resulting base of the formula I can be converted into the associated acid addition salt using an acid. For this reaction, suitable acids are those which give physiologically acceptable salts. Thus inorganic acids can be used, e.g. sulfuric acid, hydrohalic acids such as hydrochloric acid or hydrobromic acid, phosphoric acids such as orthophosphoric acid, nitric acid, sulfuric acid, furthermore organic acids, especially aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalenemono- and -disulfonic acids, laurylsulfuric acid.

If desired, the free bases of the formula I can be set free from their salts by treatment with strong bases such as sodium or potassium hydroxide, or sodium or potassium carbonate if no further acidic groups are present in the molecule. In those cases where the compounds of the formula I have free acid groups, salt formation can likewise be achieved by treatment with bases. Suitable bases are alkali metal hydroxides, alkaline earth metal hydroxides or organic bases in the form of primary, secondary or tertiary amines.

The invention further relates to the use of the compounds of the formula I and their physiologically acceptable salts for the production of pharmaceutical preparations, in particular in a non-chemical manner. In this connection, they can be brought into a suitable dose form together with at least one solid, liquid or semi-liquid excipient or auxiliary and, if appropriate, in combination with one or more other active compounds.

The invention further relates to compositions, in particular pharmaceutical preparations, comprising at least one compound of the formula I and/or one of its physiologically acceptable salts. These preparations can be employed as medicaments in human and veterinary medicine. Possible excipients are organic or inorganic substances which are suitable for enteral (e.g. oral) or parenteral administration or topical application and do not react with the novel compounds, for example water, vegetable oils, benzyl alcohols, polyethylene glycols, gelatin, carbohydrates such as lactose or starch, magnesium stearate, talc, petroleum jelly. In particular, tablets, coated tablets, capsules, syrups, juices, drops or suppositories are used for enteral administration, solutions, preferably oily or aqueous solutions, and furthermore suspensions, emulsions or implants are used for parenteral administration, and ointments, creams or powders are used for topical application. The novel compounds can also be lyophilized and the resulting lyophilizates used, for example, for the production of injection preparations.

The preparations indicated can be sterilized and/or contain auxiliaries such as lubricants, preservatives, stabilizers and/or wetting agents, emulsifiers, salts for affecting the osmotic pressure, buffer substances, colourants, flavourings and/or aromatizers. If desired, they can also contain one or more other active compounds, e.g. one or more vitamins.

The compounds of the formula I and their physiologically acceptable salts can be used in the therapeutic treatment of the human or animal body and in the control of illnesses. They are suitable for the treatment of disorders of the central nervous system such as states of tension, depression, anxiety states, schizophrenia, gastrointestinal tract disorders, nausea, tardive dyskinesias, Parkinsonism and/or psychoses and of side effects in the treatment of hypertension (e.g. with (α-methyldopa). The compounds can further be used in endocrinology and gynaecology, e.g. for the therapy of acromegaly, hypogonadism, secondary amenorrhoea, premenstrual syndrome, undesired puerperal lactation, and furthermore for the prophylaxis and therapy of cerebral disorders (e.g. migraine), in particular in geriatrics, similar to certain ergot alkaloids.

Particularly preferably, they can also be employed as therapeutics for the control of the sequelae of cerebral infarcts (cerebral apoplexy), such as stroke and cerebral ischaemias and for the treatment of brain and spinal cord traumata.

In particular, however, they are suitable as pharmaceutical active compounds for anxiolytics, antidepressants, antipsychotics and/or for positively affecting obsessive-compulsive disorder (OCD), sleep disorders, tardive dyskinesias, learning disorders, age-dependent memory disorders, eating disorders such as bulimia and/or sexual function disorders.

In this case, as a rule the substances according to the invention are administered in analogy to known, commercially available preparations (e.g. bromocriptine, dihydroergocornine), preferably in doses between approximately 0.2 and 500 mg, in particular between 0.2 and 50 mg per dose unit. The daily dose is preferably between approximately 0.001 and 10 mg/kg of body weight. The low doses are between approximately 0.2 and 500 mg, in particular between 0.2 and 50 mg, per dose unit. The low doses (approximately 0.2 to 1 mg per dose unit; approximately 0.001 to 0.005 mg/kg of body weight) are in this case suitable in particular for use as anti-migraine agents; for the other indications doses of between 10 and 50 mg per dose unit are preferred. The specific dose for each intended patient depends, however, on all sorts of factors, for example on the efficacy of the specific compound employed, on the age, body weight, general state of health and sex, and on the diet, on the time and route of administration, on the excretion rate, pharmaceutical combination and severity of the particular disorder to which the therapy applies. Oral administration is preferred.

Above and below, all temperatures are indicated in ° C. In the examples below, "customary working up" means: if necessary, water is added, the mixture is adjusted, if necessary, depending on the constitution of the final product, to a pH of between 2 and 10, and extracted with ethyl acetate or dichloromethane, the extract is separated off, the organic phase is dried over sodium sulfate, filtered and evaporated, and the residue is purified by chromatography or silica gel and/or by crystallization. $R_f$ values were obtained by thin-layer chromatography on silica gel. $M^+ +1$ values were determined by FAB-MS (Fast Atom Bombardment Mass Spectroscopy).

EXAMPLE 1

0.79 g (0.003 mol) of 4-(2-oxo-2H-1-benzopyran-4-yl) piperazine [obtainable, for example, by reaction of N,N-bis (2-chloroethyl) amine with 4-amino-2-oxo-2H-1-benzopyran] and 0.80 g (0.003 mol) of 3-(4-chloro-butyl)-5-cyanoindole [which can be prepared by reduction of 3-(4-chlorobutanoyl) indole-5-carbonitrile] are dissolved in 100 ml of acetonitrile, 0.50 ml (0.004 mol) of triethylamine and 1.20 ml (0.007 mol) of ethyldiisopropylamine are added, and the mixture is stirred overnight on a steam bath. After customary working up, 3-{4-[4-(2-oxo-2H-1-benzopyran-4-yl)-1-piperazinyl]butyl}indole-5-carbonitrile, dihydrochloride, m.p. 284–285°, is obtained.

The following are prepared analogously:

3-{4-[4-(2-oxo-2H-1-benzopyran-4-yl)-1-piperazinyl]-butyl}indole,

3-{4-[4-(2-oxo-2H-1-benzopyran-4-yl)-1-piperazinyl]-butyl}-5-fluoroindole,

3-{4-[4-(2-oxo-2H-1-benzopyran-4-yl)-1-piperazinyl]-butyl}-5-chloroindole,

3-{4-[4-(2-oxo-2H-1-benzopyran-4-yl)-1-piperazinyl]-butyl}-5-methoxyindole,

3-{4-[4-(2-oxo-2H-1-benzopyran-4-yl)-1-piperazinyl]-butyl}-5-ethoxyindole, methyl 3-{4-[4-(2-oxo-2H-1-benzopyran-4-yl)-1-piperazinyl]butyl}indole-5-carboxylate, 3-{4-[4-(2-oxo-2H-1-benzopyran-4-yl)-1-piperazinyl]-butyl}-6-fluoroindole, 3-{4-[4-(2-oxo-2H-1-benzopyran-4-yl)-1-piperazinyl]-butyl}-6-chloroindole, 3-{4-[4-(2-oxo-2H-1-benzopyran-4-yl)-1-piperazinyl]-butyl}-6-methoxyindole, 3-{4-[4-(2-oxo-2H-1-benzopyran-4-yl)-1-piperazinyl]-butyl}-6-ethoxyindole, methyl 3-{4-[4-(2-oxo-2H-1-benzopyran-4-yl)-1-piperazinyl]butyl}indole-6-carboxylate, 3-{4-[4-(2-oxo-2H-1-benzopyran-4-yl)-1-piperazinyl]-butyl}indole-6-carbonitrile.

EXAMPLE 2

A mixture of 8.3 g (0.031 mol) of 4-(2-oxo-2H-1-benzopyran-6-yl)piperazine, hydrochloride (preparation as mentioned in Example 1), 7.70 g (0.033 mol) of 3-(4-chlorobutyl)-5-cyanoindole (preparation see Example 1), 6.7 g (0.066 mol) of triethylamine, 11.3 ml (0.066 mol) of ethyldiisopropylamine and 55 ml of 1-methyl-2-pyrrolidone is stirred overnight at a bath temperature of 120–130°. The suspension is then stirred into 4 l of ice water and, after stirring for a relatively long time, crystalline 3-{4-[4-(2-oxo-2H-1-benzopyran-6-yl)-1-piperazinyl]butyl}indole-5-carbonitrile, m.p. 135–137°, is obtained as the dihydrochloride, m.p. 282–284°.

The following are prepared analogously:

3-{4-[4-(2-oxo-2H-1-benzopyran-6-yl)-1-piperazinyl]-butyl}indole,

3-{4-[4-(2-oxo-2H-1-benzopyran-6-yl)-1-piperazinyl]-butyl}indole-5-carbonitrile, monohydrochloride, m.p. 287–290°, 3-{4-[4-(2-oxo-2H-1-benzopyran-6-yl)-1-piperazinyl]-butyl}-5-methoxyindole, 3-{4-[4-(2-oxo-2H-1-benzopyran-6-yl)-1-piperazinyl]-butyl}-5-ethoxyindole, methyl 3-{4-[4-(2-oxo-2H-1-benzopyran-6-yl)-1-piperazinyl]butyl}indole-5-carboxylate, 3-{4-[4-(2-oxo-2H-1-benzopyran-6-yl)-1-piperazinyl]-butyl}-6-methoxyindole, 3-{4-[4-(2-oxo-2H-1-benzopyran-6-yl)-1-piperazinyl]-butyl}-6-ethoxyindole, methyl 3-{4-[4-(2-oxo-2H-1-benzopyran-6-yl)-1-piperazinyl]butyl}indole-6-carboxylate, 3-{4-[4-(2-oxo-2H-1-benzopyran-6-yl)-1-piperazinyl]-butyl}indole-6-carbonitrile.

EXAMPLE 3

A mixture of 5.10 g (0.017 mol) of 4-(5-fluoroindol-3-yl)butyl methanesulfonate [obtainable by reaction of 4-(5-fluoroindol-3-yl)butanol (obtainable by lithium aluminium hydride reduction of 4-(5-fluoroindol-3-yl)butanoic acid, which can be prepared analogously to a Japp-Klingemann reaction, in THF) with methanesulfonyl chloride], 4.0 g (0.015 mol) of 4-(2-oxo-2H-1-benzopyran-6-yl)piperazine, hydrochloride (obtainable as described in Example 1), 200 ml of acetonitrile and 10.0 ml of triethylamine is reacted for 30 hours on a steam bath with stirring. After customary working up, 3-{4-[4-(2-oxo-2H-1-benzopyran-6-yl)-1-piperazinyl]butyl}-5-fluoroindole, hydrochloride, m.p. 293–295°, is obtained.

The following are prepared analogously:

3-{4-[4-(2-oxo-2H-1-benzopyran-6-yl)-1-piperazinyl]-butyl}-5-chloroindole,

3-{4-[4-(2-oxo-2H-1-benzopyran-6-yl)-1-piperazinyl]-butyl}-6-fluoroindole,

3-{4-[4-(2-oxo-2H-1-benzopyran-6-yl)-1-piperazinyl]-butyl}-6-chloroindole,

3-{4-[4-(7-hydroxy-2-oxo-2H-1-benzopyran-6-yl)-1-piperazinyl]butyl}indole,

3-{4-[4-(7-hydroxy-2-oxo-2H-1-benzopyran-6-yl)-1-piperazinyl]butyl}-5-fluoroindole,
3-{4-[4-(7-hydroxy-2-oxo-2H-1-benzopyran-6-yl)-1-piperazinyl]butyl}-6-fluoroindole,
3-{4-[4-(7-hydroxy-2-oxo-2H-1-benzopyran-6-yl)-1-piperazinyl]butyl}-5-chloroindole,
3-{4-[4-(7-hydroxy-2-oxo-2H-1-benzopyran-6-yl)-1-piperazinyl]butyl}-6-chloroindole.

EXAMPLE 4

A mixture of 0.0098 mol of 4-(5-methoxycarbonylindol-3-yl)butyl methanesulfonate (preparation as described in Example 3) and 0.0097 mol of 4-(2-oxo-2H-1-benzopyran-6-yl)piperazine is heated in acetonitrile for about 96 hours on a steam bath. The reaction mixture is worked up in the customary manner and purified. Methyl 3-{4-[4-(2-oxo-2H-1-benzopyran-6-yl)-1-piperazinyl]-butyl}indole-5-carboxylate is thus obtained.

The following are obtained analogously:

methyl 3-{4-[4-(7-methyl-2-oxo-2H-1-benzopyran-6-yl)-1-piperazinyl]butyl}indole-5-carboxylate
methyl 3-{4-[4-(7-methoxy-2-oxo-2H-1-benzopyran-6-yl)-1-piperazinyl]butyl}indole-5-carboxylate
methyl 3-{4-[4-(7-fluoro-2-oxo-2H-1-benzopyran-6-yl)-1-piperazinyl]butyl}indole-5-carboxylate
methyl 3-{4-[4-(7-chloro-2-oxo-2H-1-benzopyran-6-yl)-1-piperazinyl]butyl}indole-5-carboxylate
methyl 3-{4-[4-(7-cyano-2-oxo-2H-1-benzopyran-6-yl)-1-piperazinyl]butyl}indole-5-carboxylate
methyl 3-{4-[4-(7-methyl-2-oxo-2H-1-benzopyran-4-yl)-1-piperazinyl]butyl}indole-5-carboxylate
methyl 3-{4-[4-(7-methoxy-2-oxo-2H-1-benzopyran-4-yl)-1-piperazinyl]butyl}indole-5-carboxylate
methyl 3-{4-[4-(7-fluoro-2-oxo-2H-1-benzopyran-4-yl)-1-piperazinyl]butyl}indole-5-carboxylate
methyl 3-{4-[4-(7-chloro-2-oxo-2H-1-benzopyran-4-yl)-1-piperazinyl]butyl}indole-5-carboxylate
methyl 3-{4-[4-(7-cyano-2-oxo-2H-1-benzopyran-4-yl)-1-piperazinyl]butyl}indole-5-carboxylate
methyl 3-{4-[4-(2-oxo-2H-1-benzopyran-6-yl)-1-piperazinyl]butyl}indole-6-carboxylate
methyl 3-{4-[4-(7-methyl-2-oxo-2H-1-benzopyran-6-yl)-1-piperazinyl]butyl}indole-6-carboxylate
methyl 3-{4-[4-(7-methoxy-2-oxo-2H-1-benzopyran-6-yl)-1-piperazinyl]butyl}indole-6-carboxylate
methyl 3-{4-[4-(7-fluoro-2-oxo-2H-1-benzopyran-6-yl)-1-piperazinyl]butyl}indole-6-carboxylate
methyl 3-{4-[4-(7-chloro-2-oxo-2H-1-benzopyran-6-yl)-1-piperazinyl]butyl}indole-6-carboxylate
methyl 3-{4-[4-(7-cyano-2-oxo-2H-1-benzopyran-6-yl)-1-piperazinyl]butyl}indole-6-carboxylate
methyl 3-{4-[4-(7-methyl-2-oxo-2H-1-benzopyran-4-yl)-1-piperazinyl]butyl}indole-6-carboxylate
methyl 3-{4-[4-(7-methoxy-2-oxo-2H-1-benzopyran-4-yl)-1-piperazinyl]butyl}indole-6-carboxylate
methyl 3-{4-[4-(7-fluoro-2-oxo-2H-1-benzopyran-4-yl)-1-piperazinyl]butyl}indole-6-carboxylate
methyl 3-{4-[4-(7-chloro-2-oxo-2H-1-benzopyran-4-yl)-1-piperazinyl]butyl}indole-6-carboxylate
methyl 3-{4-[4-(7-cyano-2-oxo-2H-1-benzopyran-4-yl)-1-piperazinyl]butyl}indole-6-carboxylate.

EXAMPLE 5

1.8 g of methyl 3-{4-[4-(2-oxo-2H-1-benzopyran-6-yl)-1-piperazinyl]butyl}indole-5-carboxylate are boiled for 30 minutes with 100 ml of 2N ethanolic KOH and worked up in the customary manner and 3-{4-[4-(2-oxo-2H-1-benzopyran-6-yl)-1-piperazinyl]butyl}indole-5-carboxylic acid is obtained.

The following are obtained analogously:

3-{4-[4-(2-oxo-2H-1-benzopyran-6-yl)-1-piperazinyl]butyl}indole-6-carboxylic acid
3-{4-[4-(2-oxo-2H-1-benzopyran-4-yl)-1-piperazinyl]butyl}indole-5-carboxylic acid
3-{4-[4-(2-oxo-2H-1-benzopyran-4-yl)-1-piperazinyl]butyl}indole-6-carboxylic acid
3-{4-[4-(7-methyl-2-oxo-2H-1-benzopyran-6-yl)-1-piperazinyl]butyl}indole-5-carboxylic acid
3-{4-[4-(7-methoxy-2-oxo-2H-1-benzopyran-6-yl)-1-piperazinyl]butyl}indole-5-carboxylic acid
3-{4-[4-(7-fluoro-2-oxo-2H-1-benzopyran-6-yl)-1-piperazinyl]butyl}indole-5-carboxylic acid
3-{4-[4-(7-chloro-2-oxo-2H-1-benzopyran-6-yl)-1-piperazinyl]butyl}indole-5-carboxylic acid
3-{4-[4-(7-cyano-2-oxo-2H-1-benzopyran-6-yl)-1-piperazinyl]butyl}indole-5-carboxylic acid
3-{4-[4-(7-methyl-2-oxo-2H-1-benzopyran-4-yl)-1-piperazinyl]butyl}indole-5-carboxylic acid
3-{4-[4-(7-methoxy-2-oxo-2H-1-benzopyran-4-yl)-1-piperazinyl]butyl}indole-5-carboxylic acid
3-{4-[4-(7-fluoro-2-oxo-2H-1-benzopyran-4-yl)-1-piperazinyl]butyl}indole-5-carboxylic acid
3-{4-[4-(7-chloro-2-oxo-2H-1-benzopyran-4-yl)-1-piperazinyl]butyl}indole-5-carboxylic acid
3-{4-[4-(7-cyano-2-oxo-2H-1-benzopyran-4-yl)-1-piperazinyl]butyl}indole-5-carboxylic acid
3-{4-[4-(7-methyl-2-oxo-2H-1-benzopyran-6-yl)-1-piperazinyl]butyl}indole-6-carboxylic acid
3-{4-[4-(7-methoxy-2-oxo-2H-1-benzopyran-6-yl)-1-piperazinyl]butyl}indole-6-carboxylic acid
3-{4-[4-(7-fluoro-2-oxo-2H-1-benzopyran-6-yl)-1-piperazinyl]butyl}indole-6-carboxylic acid
3-{4-[4-(7-chloro-2-oxo-2H-1-benzopyran-6-yl)-1-piperazinyl]butyl}indole-6-carboxylic acid
3-{4-[4-(7-cyano-2-oxo-2H-1-benzopyran-6-yl)-1-piperazinyl]butyl}indole-6-carboxylic acid
3-{4-[4-(7-methyl-2-oxo-2H-1-benzopyran-4-yl)-1-piperazinyl]butyl}indole-6-carboxylic acid
3-{4-[4-(7-methoxy-2-oxo-2H-1-benzopyran-4-yl)-1-piperazinyl]butyl}indole-6-carboxylic acid
3-{4-[4-(7-fluoro-2-oxo-2H-1-benzopyran-4-yl)-1-piperazinyl]butyl}indole-6-carboxylic acid
3-{4-[4-(7-chloro-2-oxo-2H-1-benzopyran-4-yl)-1-piperazinyl]butyl}indole-6-carboxylic acid
3-{4-[4-(7-cyano-2-oxo-2H-1-benzopyran-4-yl)-1-piperazinyl]butyl}indole-6-carboxylic acid.

The following examples relate to pharmaceutical preparations:

Example A

Injection Vials

A solution of 100 g of an active compound of the formula I and 5 g of disodium hydrogenphosphate in 3 l of double-distilled water is adjusted to pH 6.5 using 2N hydrochloric acid, sterile-filtered, filled into injection vials, lyophilized and aseptically sealed. Each injection vial contains 5 mg of active compound.

Example B

Suppositories

A mixture of 20 g of an active compound of the formula I is fused with 100 g of soya lecithin and 1400 g of cocoa butter, poured into moulds and allowed to cool. Each suppository contains 20 mg of active compound.

Example C

Solution

A solution of 1 g of an active compound of the formula I, 9.38 g of NaH$_2$PO$_4$×2 H$_2$O, 28.48 g of NaH$_2$PO$_4$×12 H$_2$O and 0.1 g of benzalkonium chloride in 940 ml of double-distilled water is prepared. It is adjusted to pH 6.8, made up to 1 l and sterilized by irradiation. This solution can be used in the form of eye drops.

Example D

Ointment 500 mg of an active compound of the formula I are mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

Example F

Coated Tablets

Analogously to Example E, tablets are pressed which are then coated in a customary manner with a coating of sucrose, potato starch, talc, tragacanth and colourant.

Example G

Capsules 2 kg of active compound of the formula I are dispensed in a customary manner into hard gelatin capsules such that each capsule contains 20 mg of the active compound.

Example H

Ampoules is A solution of 1 kg of active compound of the formula I in 60 l of double-distilled water is dispensed into ampoules, lyophilized under aseptic conditions and aseptically sealed. Each ampoule contains 10 mg of active compound.

What is claimed is:

1. A compound of the formula I

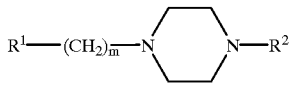

I in which
- R$^1$ is an indol-3-yl radical which is unsubstituted or mono- or disubstituted by Hal, CN, A, AO, OH, CONH$_2$, CONHA, CONA$_2$, COOH, COOA, CH$_2$OH, CH$_2$OA, CH$_2$NH$_2$, CH$_2$NHA, CH$_2$NA$_2$, or combinations thereof;
- R$^2$ is 2-oxo-2H-1-benzopyran-6-yl or 2-oxo-2H-1-benzopyran-4-yl, which is unsubstituted or mono- or disubstituted by A, AO, OH, Hal, CN, NO$_2$, NH$_2$, NHA, NA$_2$, COA, CONH$_2$, CONHA, CONA$_2$, CH$_2$OH, CH$_2$OA, CH$_2$NH$_2$, CH$_2$NHA, CH$_2$NA$_2$, COOH, COOA, or combinations thereof;

Hal is F, Cl, Br or I;

A is straight-chain or branched alkyl having 1–10 C atoms, which is unsubstituted or substituted by 1 to 5 F atoms Cl atoms, or combinations thereof, or is cycloalkyl having 3–10 C atoms; and m is 2, 3 or 4; or a physiologically acceptable salt thereof.

2. A compound according to claim 1, wherein said compound is:
   a) 3-{4-[4-(2-oxo-2H-1-benzoypyran-6-yl)-1-piperazinyl]butyl}indole-5-carbonitrile, or a physiologically acceptable salt thereof;
   b) 3-{4-[4-(2-oxo-2H-1-benzoypyran-6-yl)-1-piperazinyl]butyl}-5-fluoroindole, or a physiologically acceptable salt thereof;
   c) 3-{4-[4-(2-oxo-2H-1-benzoypyran-4-yl)-1-piperazinyl]butyl}indolel-5-carbonitrile, or a physiologically acceptable salt thereof; or
   d) 3-{4-[4-(7-hydroxyl-2-oxo-2H-1-benzoypyran-6-yl)-1-piperazinyl]butyl}indole-5-carbonitrile or a physiologically acceptable salt thereof.

3. A compound according to claim 1, wherein A is methyl, ethyl, n-propyl, isopropyl, n-butyl, sec-butyl, tert-butyl, pentyl, 1-, 2- or 3-methylbutyl, 1,1-, 1,2- or 2,2-dimethylpropryl, 1-ethylpropyl, hexyl, 1-, 2-, 3- or 4-methylpentyl, 1,1-, 1,2-, 1,3-, 2,2-, 2,3- or dimethylbutyl, 1- or 2-ethylbutyl, 1-ethyl-1-methylpropyl, 1-ethyl-2-methylpropyl, 1,1,2- or 1,2,2-trimethylpropyl, fluoromethyl, difluoromethyl, trifluuoromethyl, 1,1,1-trichloroethyl, pentafluoroethyl, cyclopropyl, cyclobutyl, cyclopentyl, cyclohexyl, cycloheptyl or 1-adamantyl.

4. A compound according to claim 1, wherein Hal is fluorine or chlorine.

5. A compound according to claim 1, wherein m is 3 or 4.

6. A compound according to claim 1, wherein R$^1$ is 3-indolyl which is unsubstituted or monosubstituted by Hal, CN, A, AO, OH, CONH$_2$, CONHA, CONA$_2$, COOH, COOA, CH$_2$OH, CH$_2$OA, CH$_2$NH$_2$, CH$_2$NHA or CH$_2$NA$_2$.

7. A compound according to claim 5, wherein R$^1$ is 3-indolyl substituted in the 5 position.

8. A compound according to claim 6, wherein R$^1$ is 3-indolyl substituted in the 6 position.

9. A compound according to claim 6, wherein R$^1$ is 3-indolyl substituted in the 7 position.

10. A compound according to claim 1, wherein R$^2$ is 2-oxo-2H-1-benzo-pyran-6-yl or 2-oxo-2H-1-benzopyran-4-yl, which is unsubstituted or monosubstituted by A, AO, OH, Hal, CN, NO$_2$, NH$_2$, NHA, NA$_2$, COA, CONH$_2$, CONH$_2$, CONHA, CONA$_2$, CH$_2$OH, CH$_2$OA, CH$_2$NH$_2$, CH$_2$NHA, CH$_2$NA$_2$, COOH or COOA.

11. A compound according to claim 1, wherein R$^1$ is 3-indolyl.

12. A compound according to claim 1, wherein R$^1$ is 3-indolyl substituted by Hal, methoxycarbonyl, CN or carboxyl.

13. A compound according to claim 1, wherein R$^2$ is 2-oxo-2H-1-benzopyran-6-yl or 2-oxo-2H-1-benzopyran-4-yl, which in each case is unsubstituted or is substituted in the 7 position.

14. A compound according to claim 13, wherein R$^2$ is 2-oxo-2H-1-benzopyran-6-yl or 2-oxo-2H-1-benzopyran-4-yl, which is substituted in the 7 position by Hal or OH.

15. A process for the preparation of a compound according to claim 1, said process comprising:

reacting a compound of formula II

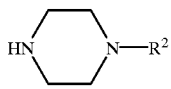
II with a compound of formula III

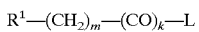
III in which
k is 0, and
L is Cl, Br, I, OH, OCOA, OCOPh, $OSO_2A$, $OSO_2Ar$, where Ar is phenyl or tolyl and A is alkyl, or another reactive esterified OH group or easily nucleophilically substitutable leaving group; or
reacting a compound of the formula IV

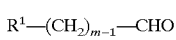
IV with a compound of the formula II; or converting a base or acid of the formula I into a pharmaceutically acceptable salt thereof by treatment with an acid or base.

16. A process for the production of a pharmaceutical preparation comprising combining a compound of claim 1 with at least one solid, liquid or semi-liquid excipient or auxiliary and, optionally, one or more other active compounds.

17. A pharmaceutical composition comprising at least one compound according to claim 1 and a pharmaceutically acceptable carrier.

18. A method of inducing an antidepressant effect in a patient comprising administering to said patient an antidepressant effective amount of a compound according to claim 1.

19. A method of inducing an anxiolytic effect in a patient comprising administering to said patient an anxiolytic effective amount of a compound according to claim 1.

* * * * *

UNITED STATES PATENT AND TRADEMARK OFFICE
CERTIFICATE OF CORRECTION

PATENT NO. : 6,251,908 B1
APPLICATION NO. : 09/462468
DATED : June 26, 2001
INVENTOR(S) : Bartoszyk It is certified that error appears in the above-identified patent and that said Letters Patent is hereby corrected as shown below:

Column 14, line 4, reads "F atoms Cl atoms" should read -- F atoms, Cl atoms, --
Column 14, line 9, reads "benzoypyran" should read -- benzopyran --
Column 14, line 12, reads "benzoypyran" should read -- benzopyran --
Column 14, line 15, reads "benzoypyran" should read -- benzopyran --
Column 14, line 16, reads "indolel" should read -- indole --
Column 14, line 18, reads "benzoypyran" should read -- benzopyran --
Column 14, line 24, reads "dimethylpropryl," should read -- dimethylpropyl, --
Column 14, line 25, reads "2,3- or dimethylbutyl." should read -- 2,3- or 3,3- dimethylbutyl. --
Column 14, line 28, reads "trifluuoromethyl," should read -- trifluoromethyl, --
Column 14, line 38, reads "according to claim 5," should read -- according to claim 6, --
Column 14, line 47, after "COA", delete -- $CONH_2$ --.

Signed and Sealed this

Fifteenth Day of August, 2006

JON W. DUDAS
*Director of the United States Patent and Trademark Office*